Figure 1:
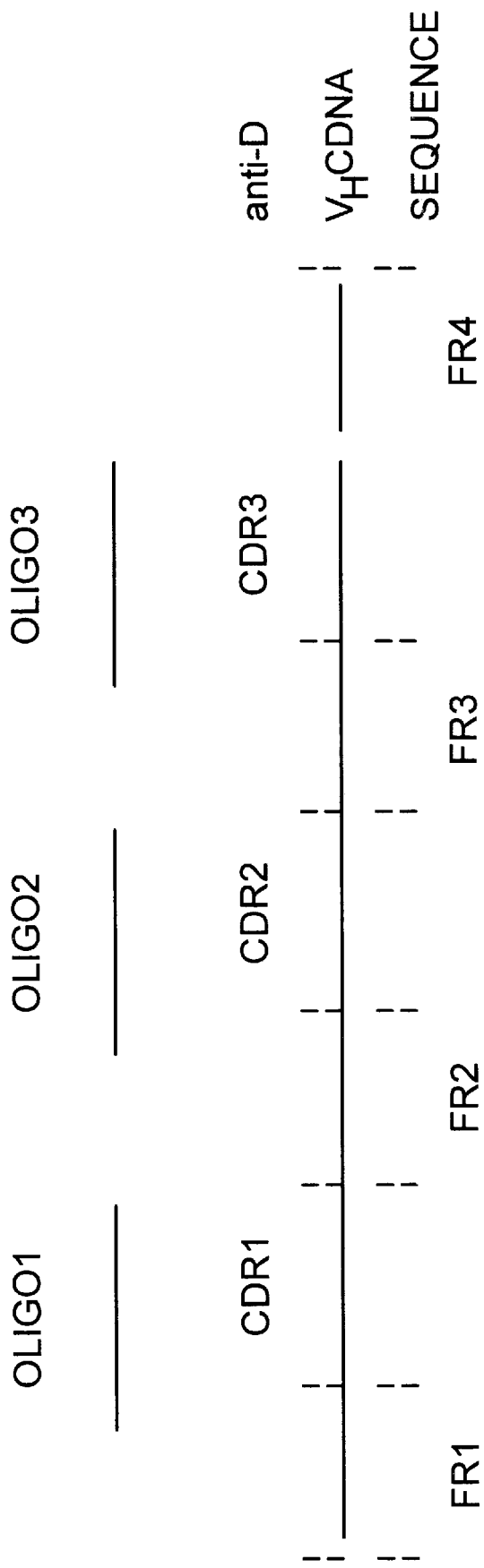
Figure 1:
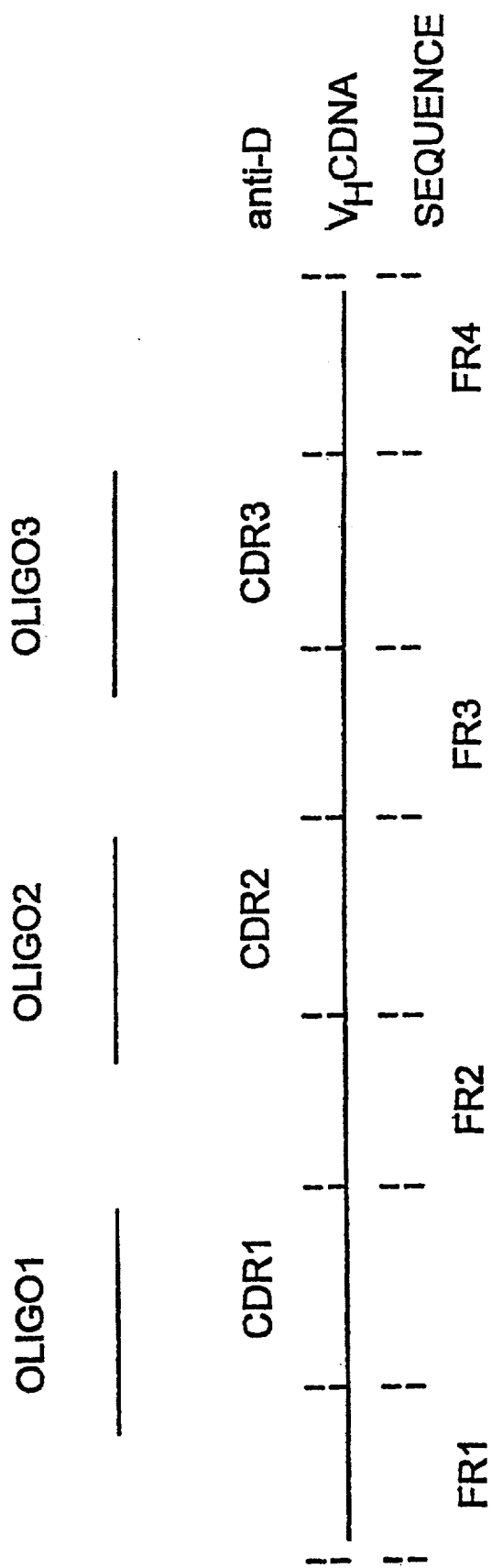

United States Patent [19]

Hughes-Jones

[11] Patent Number: 5,831,063
[45] Date of Patent: Nov. 3, 1998

[54] MONOCLONAL ANTIBODIES

[75] Inventor: Nevin Campbell Hughes-Jones, Royston, Great Britain

[73] Assignee: National Blood Authority, Watford, England

[21] Appl. No.: 856,034
[22] PCT Filed: Nov. 13, 1990
[86] PCT No.: PCT/EP90/01964
  § 371 Date: Jun. 23, 1992
  § 102(e) Date: Jun. 23, 1992
[87] PCT Pub. No.: WO91/07492
  PCT Pub. Date: May 30, 1991

[30] Foreign Application Priority Data

Nov. 13, 1989 [GB] United Kingdom .................... 8925590

[51] Int. Cl.$^6$ .................................................. C12N 15/13
[52] U.S. Cl. ...................................... 536/23.53; 435/320.1
[58] Field of Search ........................ 536/23.53; 435/320.1

[56] References Cited

FOREIGN PATENT DOCUMENTS 0239400  9/1987  European Pat. Off. .
2189506  10/1987  United Kingdom ........... C12N 15/00

OTHER PUBLICATIONS

Reichmann et al. Nature 332: 323–327 1987.
Morrison et al., *Clin. Chem.*, 34(9):1688 (Sep. 1988).
Verhoeyen et al., *Bio Essays*, 8(2):74–78 (Feb.–Mar. 1988).
Thompson K.M. et al. (1986) "Production of human monoclonal IgG and IgM antibodies with anti–D (rhesus) specificity using heterohybridomas," *Immunology* 58, 157–160.
Wiener E. et al. (1987) "Differences between the activities of human monoclonal IgG1 and IgG3 subclasses of anti–D(Rh) antibodies in their ability to mediate red cell–binding to macrophages." *Immunology* 62, 401–404.
Melamed M.D. et al. (1987) "Requirements for the establishment of heterohybridomas secreting monoclonal human antibody to rhesus (D) blood group antigen." *Journal of Immunological Methods* 104, 245–251.
Hughes–Jones N.C. et al. (1987) "Radio–immunoassy of the functional activity oa anti–D(Rh) preparations using a human monoclonal $^{125}$I–labelled anti–D." *Vox Sanguinis* 53, 175–180.
Weiner E. et al. (1988) "Differences between the activity of human monoclonal IgG1 and IgG3 anti–D antibodies of the Rh blood group system in their abilities to mediate effector functions of monocytes." *Immunology* 65, 159–163.
Hughes–Jones N.C. et al. (1988) "Evidence that the c, D and E epitopes of the human RH blood group system are on separate polypeptide molecules." *Molecular Immunology* 25, 931–936.
Gorick B.D. et al. (1988) "Three epitopes on the human Rh antigen D recognized by $^{125}$I–labelled human monoclonal IgG antibodies." *Vox Sanguinis* 55, 165–170.
McCann M.C. et al. (1988) "Production and use of human monoclonal anti–D antibodies." *Journal of Immunological Methods* 115, 3–15.
Walker M.R. et al. (1988) "Immunogenic and antigenic epitopes of immunoglobulins. Binding of human monoclonal anti–D antibodies to FeRI on the monocyte–like U937 cell line." *Vox Sanguinis* 55, 222–228.
Merry A.H. et al. (1988) "Comparison of the ability of monoclonal and polyclonal anti–D antibodies to promote the binding of erythrocytes, to lymphocytes granulocytes and monocytes." *Biochemical Society Transactions* 16, 727–728.
Jones V.E. et al. (1988) "A new assay uses monoclonal anti–Rh(D) antibodies to determine Rheumatoid factor specificity; reactivity to a monoclonal antibody of the Gm allotype G3m(21) is more frequent in rheumatoid patients negative for G3m(21)." *Clinical and Experimental Immunology* 71, 451–458.
Puttick A.H. et al. (1988) "Reaction of rheumatoid factors with IgG3 monoclonal anti–Rh(D) antibodies: more frequent reactivity to a monoclonal of the Gm allotype G3m(5) in rheumatoid patients negative for G3m(5)." *Annals of the Rheumatic Diseases* 47, 898–905.
Merry A. H. et al. (1989) "Ability of monoclonal anti–D antibodies to promote the binding of red cells to lymphocytes, granulocytes and monocytes." *Vox Sanguinis* 56, 48–53.
Lomas C. et al. (1989) "Demonstration of seven epitopes on the Rh antigen D using human monoclonal anti–D antibodies and red cells from D categories." *Vox Sanguinis* 57, 261–264.
Thorpe S.J. (1989) "Detection of Rh D–associated epitopes in human and animal tissues using human monoclonal anti–D antibodies." *British Journal of Haematology* 73, 527–536.
Kumpel B.M. et al. (1989) "Heterogeneity in the ability of IgG1 anti–D to promote lymphocyte–mediated red cell lysis." *European Journal of Immunology* 19, 2283–2288.
Hadley A.G. et al. (1989) "Synergistic effect of blending IgG1 and IgG3 monoclonal anti–D promoting the metabolic response of monocytes to sensitized red cells." *Immunology* 67, 550–552.

*Primary Examiner*—Frank C. Eisenschenk
*Attorney, Agent, or Firm*—Burns, Doane, Swecker & Mathis, L.L.P.

[57] ABSTRACT

The present invention provides DNA sequences encoding complementarity determining regions of variable domains of human anti-RhD antibodies and their use in the production of recombinant chimaeric antibody molecules.

23 Claims, 14 Drawing Sheets

```
  1 CAGTCTGTGTTGACGCAGCCGCCCTCAGTGTCTGCCCCCAGGACAGAAGGTCACCATC   60
    Q  S  V  L  T  Q  P  P  S  V  S  A  A  P  G  Q  K  V  T  I

61 TCCTGCTCCGGAACCAGTTCCAACATTGGGAATAATTATGTATCCTGGTATCAGCAGCTC  120
    S  C  S  G  T  S  S  N  I  G  N  N  Y  V  S  W  Y  Q  Q  L
                        <------ CDR1 ------>

121 CCAGGAACAGCCCCCAAACTCCTCATTTATGACAATAATAAGCGACCCTCAGGGATTCCT  180
    P  G  T  A  P  K  L  L  I  Y  D  N  N  K  R  P  S  G  I  P
                              <------ CDR2 ------>

181 GACCGATTCTCTGGCTCCAAGTCTGGCACGTCAGCCACCCTGGGCATCACCGGACTCCGG  240
    D  R  F  S  G  S  K  S  G  T  S  A  T  L  G  I  T  G  L  R

241 ACTGGGGACGAGGCCGATTATTACTGCGCAACATGGGATAGCAGCCTGAGTGCTGTGGTG  300
    T  G  D  E  A  D  Y  Y  C  A  T  W  D  S  S  L  S  A  V  V
                              <------ CDR3

301 TTCGGCGGAGGGACCAAGCTGACCGTCCTAAGT   333
    F  G  G  G  T  K  L  T  V  L  S
    ------>
```

FIG. 2

```
  1  TCCTATGTGCTGACTCAGCCACCCTCGGTGTCAGTGGCCCCAGGACAGACGGCCAGGATT  60
      S  Y  V  L  T  Q  P  P  S  V  S  V  A  P  G  Q  T  A  R  I

61  ACCTGTGGGGGAAACAACATTGGACGTAAAAGTGTGCACTGGTACCAGCAGAAGCCAGGC 120
      T  C  G  G  N  N  I  G  R  K  S  V  H  W  Y  Q  Q  K  P  G
                     <------------ CDR1 ------------>

121  CAGGCCCCTGTGCTGGTCGTCTATGGTGCTAGCGACCGGCCCTCAGGGATCCCTGAGCGA 180
      Q  A  P  V  L  V  V  Y  G  A  S  D  R  P  S  G  I  P  E  R
                              <---------- CDR2 ---------->

181  TTCTCTGGCTCCAACTCTGGGAACACGGCCACCCTGACCATCAGCAGAGTCGCAGCCGGG 240
      F  S  G  S  N  S  G  N  T  A  T  L  T  I  S  R  V  A  A  G

241  GATGAGGCCGACTATTACTGTGTCAGGTGTGGGATAGTAGTAGTGCTCATCCGGGGTGTA 300
      D  E  A  D  Y  Y  C  Q  V  W  D  S  S  S  A  H  P  G  V  V
                              <------------ CDR3 ------------->

301  TTCGGCGGAGGGACCAAGCTGACCGTCCTAGGT 333
      F  G  G  G  T  K  L  T  V  L  G
```

FIG. 3

```
  1  CAGCTGCGCGGCTGCAGGAGTCGGGCCCAGGACTGGTGAAGCCTTCGGAGACCCTGTCCCTC    60
     Q  L  R  L  Q  E  S  G  P  G  L  V  K  P  S  E  T  L  S  L

61  ACCTGCAGTGTCTCGGTGGCTCCGTCAGCAGTGTCTCTACTGGGCTGGTGGGTCCGC    120
     T  C  S  V  S  V  G  G  S  V  S  S  G  G  L  Y  W  G  W  V  R
                                          <------ CDR1 ------>

121  CAGCCCCCAGGGAAGGGGCTCGAATGGATTGGCAGTATATTTTATAGTGGAGCACCTAC    180
     Q  P  P  G  K  G  L  E  W  I  G  S  I  F  Y  S  G  S  T  Y
                                        <------------ CDR2

181  TACAATCCCTCCCTCAAGAGCCGAGTCACCATATCCGTAGACACGTTGAAGAATAACTTC    240
     Y  N  P  S  L  K  S  R  V  T  I  S  V  D  T  L  K  N  N  F
     ------------>

241  TCCCTGAAGCTGAGTTCTGTGACAGCAGCAGACACGGCTGTTTATTACTGTACGAGACCA    300
     S  L  K  L  S  S  V  T  A  A  D  T  A  V  Y  Y  C  T  R  P
                                                            <---

301  GGCTATGGCGACACCTCGGTACGGAAGAGGGTTTGGAATATGGACCTCTGGGGCCAAGGG    360
     G  Y  G  D  T  S  V  R  K  R  V  W  N  M  D  L  W  G  Q  G
     --------------------- CDR3 ---------------------->

361  ACCACGGTCACCGTCTCCTCG    381
     T  T  V  T  V  S  S
```

FIG. 4

```
  1 CAGGTGCAGCTGCAGGAGTCGGGCCCAGGACTGGTGAAGCCTTCGGAGACCCTGTCCGTC      60
    Q  V  Q  L  Q  E  S  G  P  G  L  V  K  P  S  E  T  L  S  V

61 ACCTGCACTGTCTCTGGTGGCTCCGTCAGTAGTTCCTACTGGAGCTGGATCCGGCAGCCC     120
    T  C  T  V  S  G  G  S  V  S  S  S  Y  W  S  W  I  R  P  R
                                        <----- CDR1 ----->

121 CCAGGGAAGGACCGGAGTGGATTGGGTATATCTATTACAGTGGGAGCACCAACTACAAC     180
    P  G  K  G  P  E  W  I  G  Y  I  Y  Y  S  G  S  T  N  Y  N
                                     <-------- CDR2

181 CCCTCCCTCAGGAGTCGAGTCACCATATCAGTAGACACGTCCAAGAACCAGTTCTCCCTG     240
    P  S  L  R  S  R  V  T  I  S  V  D  T  S  K  N  Q  F  S  L
    -------->

241 AAGCTGGGCTCTGTGACCGCTGCGGACACGGCCGTGTATTACTGTGCGAGAGTTTTGGTT     300
    K  L  G  S  V  T  A  A  D  T  A  V  Y  Y  C  A  R  V  L  V
                                                           <---

301 TCCCGTACGATTTCACAGTACTCCTATTACATGGACGTCTGGGGCAAAGGGACCACGGTC     360
    S  R  T  I  S  Q  Y  S  Y  Y  M  D  V  W  G  K  G  T  T  V
    --------- CDR3 --------->

361 ACCGTGTCCTCA     372
    T  V  S  S
```

FIG. 5

```
  1   ------PCR PRIMER------       CGCAGGACTGTTGAAGCCTTCGGAGACCCTGTCCCTC  60
                                    A  G  L  L  K  P  S  E  T  L  S  L

61   ACCTGCGCTGTCTATGGGTCCTTCAGTGGTTACTACTGGAGCTGGATCCGCCAGCCT        120
       T  C  A  V  Y  G  G  S  F  S  G  Y  Y  W  S  W  I  R  Q  P
                                         <------ CDR1 ------>

121   CCAGGGAAGGGGCTGGAGTGGATTGGGGAAATCAATCATAGTGGAAGGACCAACTACAAC     180
       P  G  K  G  L  E  W  I  G  E  I  N  H  S  G  R  T  N  Y  N
                                    <------------ CDR2

181   CCGTCCCTCAAGACTCGAGTCACCATATCAGTAGACACGTCCAAGAACCAGTTCTCCCTG     240
       P  S  L  K  T  R  V  T  I  S  V  D  T  S  K  M  Q  F  S  L
                       ------------>

241   AAGCTGAGTTCTGTGACCGCCGCGGACACGGCTGTGTATTACTGTGCGAGACTGTGGCTC    300
       K  L  S  S  V  T  A  A  D  T  A  V  Y  Y  C  A  R  L  W  L
                                                            <----

301   GATGGACATGGGTACAAGTTTGACTACTGGGGCCAGGGAACCCT    ------PCR PRIMER------  360
       D  G  H  G  Y  K  F  D  Y  W  G  Q  G  T  L
       ------------ CDR3 ------------>
```

FIG. 6

```
  1 CAGGTGCATCTACAGCAGTGGGGCACAGGCTGTGAAGCCTTCGGAGACCCTGTCCCTC    60
    Q  V  H  L  Q  Q  W  G  T  G  L  L  K  P  S  E  T  L  S  L

61 ACCTGCGCTGTGTCCTTCAATGTTTACTACTGGAACCTGGATCCGGCCAGCCC         120
    T  C  A  V  H  G  G  S  F  N  V  Y  Y  W  T  W  I  R  Q  P
                           <------- CDR1 ------->

121 CCAGGAAAGGCGCTGGAGTGGATGGGAAATCAATCATAGTGGAGGCGCCAACTACAAT    180
    P  G  K  A  L  E  W  I  G  E  I  N  H  S  G  G  A  N  Y  N
                              <-------- CDR2

181 CCGTCCCTCAAGAGTCGAGTCACCATGTCAGCAGACACGTCCAAGAACCAGTTCTCCTG    240
    P  S  L  K  S  R  V  T  M  S  A  D  T  S  K  N  Q  F  S  L
    ------->

241 AAACTGACCTCTGTGACCGCCGCGGACACGGCCGTGTATTATTGTGCGAGAGGCCGGTCC    300
    K  L  T  S  V  T  A  A  D  T  A  V  F  Y  C  A  R  G  R  S
                                                        <-----

301 CGTTATAGTGGTTACGGCTTCTACTCCGGCATGGACGTCTGGGGCCCAGGGACCACGGTC    360
    R  Y  S  G  Y  G  F  Y  S  G  M  D  V  W  G  P  G  T  T  V
    ---------------- CDR3 -------------->

361 ACCGTCTCCTCA    372
    T  V  S  S
```

FIG. 7

```
1   CAGGTGCAGCTACAGCAGTGGGGCGCAGGACTGTTGAAGCCTTCGGAGACCCTGTCCCTC   60
     Q  V  Q  L  Q  Q  W  G  A  G  L  L  K  P  S  E  T  L  S  L

61  ACCTGCGCTGTCTATGGTGGGTCCTTCAGTGGTTACTACTGGAACTGGATCCGCCAGCCC  120
     T  C  A  V  Y  G  G  S  F  S  G  Y  Y  W  N  W  I  R  Q  P
                            <------ CDR1 ------>

121 CCAGGGAAGGGGCTGGAGTGGATTGGGGAAATCATTCATAGTGGAAGCACCAACTACAAC  180
     P  G  K  G  L  E  W  I  G  E  I  I  H  S  G  S  T  N  Y  N
                                   <------ CDR2

181 CCGTCCCTCAAGAGTCGAGTCACCATGTCAGTAGACACGTCCAAGAACCAGTTCTCCCTG  240
     P  S  L  K  S  R  V  T  M  S  V  D  T  S  K  N  Q  F  S  L
              ------>

241 AAGCTGAGCTCTGTGACCGCGGCGGACACGGCTGTGTATTACTGTGCGAGAGGCTTAGAA  300
     K  L  S  S  V  T  A  A  D  T  A  V  Y  Y  C  A  R  G  L  E
                                                       <------

301 CGTCCGATTAGGAACCAGCTGCTAAACCGTCTCGGTTACTACATGGACGTCTGGGGCAAA  360
     R  P  I  R  N  Q  L  L  N  R  L  G  Y  Y  M  D  V  W  G  K
     ------------------ CDR3 ------------------>

361 GGGACCACGGTCACCGTCTCCTCA  384
     G  T  T  V  T  V  S  S

FIG. 8
```

```
  1 CAGGTGCAGCTACAGCAGTGGGGCGCAGGACTGTTGAAGCCTTCGGAGACCCTGTCCCTC    60
    Q  V  Q  L  Q  Q  W  G  A  G  L  L  K  P  S  E  T  L  S  L

61 ACCTGCGCTGTCTATGGTGGGTCCTTCAGTGGTTACTACTGGAGCTGGATCCGCCAGCCC   120
    T  C  A  V  Y  G  G  S  F  S  G  Y  Y  W  S  W  I  R  Q  P
                                  <------ CDR1 ------>

121 CCAGGGAAGGGGCTGGAGTGGATTGGGGAAATCAGTCGTCGTGGAAGCACCAACTACAAC   180
    P  G  K  G  L  E  W  I  G  E  I  S  R  R  G  S  T  N  Y  N
                                     <------- CDR2 ---------

181 CCGTCCCTCAAGAGTCGAGTCGCCATATCAGTAGACACGTCCAAGAACCAGTTCTCCCTG   240
    P  S  L  K  S  R  V  A  I  S  V  D  T  S  K  N  Q  F  S  L
    -------->

241 AAGGTGAGGTCTGTGACCGCCGCGGACACGGCTGTGTATTACTGTGCGAGAGCCTTGGAC   300
    K  V  R  S  V  T  A  A  D  T  A  V  Y  Y  C  A  R  A  L  D
                                                          <---

301 TACATCTCCTTGGATTACGGTATGGACGTCTGGGGCCAAGGGACCACGGTCACCGTCTCC   360
    Y  I  S  L  D  Y  G  M  D  V  W  G  Q  G  T  T  V  T  V  S
    ------ CDR3 ------>

361 TCA  363
    S
```

FIG. 9

```
1    -----PCR PRIMER-------   GGGAGGCGTGGTCCAGCCTGGGAGGTTCCTGAGACTC    60
                              G  G  V  V  Q  P  G  R  F  L  R  L

61   TCCTGTGCAGCGGTCTGGATTCACCTTCAGTAGCTATGGCATGCACTGGGTCCGCCAGGCT   120
      S  C  A  A  S  G  F  T  F  S  S  Y  G  M  H  W  V  R  Q  A
                                   <------ CDR1 ------>

121  CCAGGCAAGGGGCTGGAGTGGGTGGCACTTATATGGTATGATGGAAGTAATAAAGAATAT    180
      P  G  K  G  L  E  W  V  A  L  I  W  Y  D  G  S  N  K  E  Y
                                   <------ CDR2 ------

181  GCAGACTTCGTGAAGGGCCGATTCACCATCTCCAGAGACAATTCCAAGAATACACTGTAT    240
      A  D  F  V  K  G  R  F  T  I  S  R  D  N  S  K  N  T  L  Y
                                ------>

241  CTGCAAATGAACAGCCTGAGAGCCGAGGACACGGCTGTGTATTACTGTGCGACAGATAGT    300
      L  Q  M  N  S  L  R  A  E  D  T  A  V  Y  Y  C  A  T  D  S
                                                              <---

301  CCCAAAATGAGGGCTGGAAGTATGTTTCGGTTTTTTACATGGACGTCTGGGGCAAAGGG    360
      P  K  M  R  A  G  S  M  F  R  Y  Y  Y  M  D  V  W  G  K  G
     --------------------------- CDR3 --------------------->

361  ACCAC -----PCR PRIMER-----    381
      T

FIG. 10
```

```
  1 ------PCR PRIMER------  GGGAGGCTTAGTTCAGCCTGGGGGGTCCCTGAGACTC          60
                             G  G  L  V  Q  P  G  G  S  L  R  L

61 TCCTGTGCAGCCTCTGGATTCACCTTCAGTAGTTACTGGATGCACTGGGTCCGCCAAGCT         120
     S  C  A  A  S  G  F  T  F  S  S  Y  W  M  H  W  V  R  Q  A
                                  <------ CDR1 ------>

121 CCAGGGAAGGGGCTGGTGTGGGTCTCACGTATTAATAGTTATGGAATTAGCACAAGTTAC         180
     P  G  K  G  L  V  W  V  S  R  I  N  S  Y  G  I  S  T  S  Y
                                  <------- CDR2 -------

181 GCGAACTCCGTGAAGGGCCGATTCACCATCTCCAGAGACAACGCCAAGAACACGCTGTAT         240
     A  N  S  V  K  G  R  F  T  I  S  R  D  N  A  K  N  T  L  Y
     ------>

241 CTGCAAATGAACACTCTGAGAGGGGAGGACACGGTCTGTGCAAGAGAGGAGAG               300
     L  Q  M  N  T  L  R  A  E  D  T  A  V  Y  Y  C  A  R  G  E
                                                              <---

301 CGGCATAGCAGCTCGTCTCTTGTCGGGGGCGGGTACGGTATGGACGTCTGGGGCCAAGGGACC    360
     R  I  A  A  R  L  L  S  G  G  Y  G  M  D  V  W  G  Q  G  T
     -------------- CDR3 ------------->

361 AC   ------PCR PRIMER------   378
```

FIG. 11

```
  1   ———PCR PRIMER———            GGGAGGCGTGGTCCAGCCTGGAGGTCCCTGAGACTC    60
                                   G  G  V  V  Q  P  G  G  P  E  T  L

61   TCCTGTGCAGCCTCTGGATTCACCTTTAGTAGCTATGGCATGCACTGGGTTCCGCCAGGCT       120
       S  C  A  A  S  G  F  T  F  S  S  Y  G  M  H  W  V  R  Q  A
                                  <——————— CDR1 ———>

121   CCAGGCAAGGGGCTGGAGTGGGTGGCAGTGATATGGTATGATGGAAGTAATAAGTACTAT       180
       P  G  K  G  L  E  W  V  A  V  I  W  Y  D  G  S  N  K  Y  Y
                                  <————————————— CDR2

181   GCAGAGTCCGTGAAGGGGCGATTCACCATCTCCAGAGACAATTCCAAGAACACGCTGTAT       240
       A  E  S  V  K  G  R  F  T  I  S  R  D  N  S  K  N  T  L  Y
                 —————————>

241   CTGCAAATGAACAGCCTGAGAGCCGAGGACACGGCTGTGTATTACTGTGCGAGAGTCGTT       300
       L  Q  M  N  S  L  R  A  E  D  T  A  V  Y  Y  C  A  R  V  V
                                                              <———

301   AGCAGCAACCGGTACTCTCTAAGCTACTATTATTACTACATGGACGTCTGGGGCAAAGGG       360
       S  S  N  R  Y  S  L  S  Y  Y  Y  Y  Y  M  D  V  W  G  K  G
      ———————————————— CDR3 ————————————————>

361   ACCAC     ———PCR PRIMER———  381
       T
```

FIG. 12

```
1    ------PCR PRIMER------    GGGAGGCGTGTGGTCCAGCCTGGGAGGTCCCTGAGACTC    60
                               G  G  V  V  Q  P  G  R  S  L  R  L

61   TCCTGTGCAGCGGTCTGGATTCACCTTCAATAATTATGGCATGCACTGGGTCCGCCAGGCT    120
     S  C  A  A  S  G  F  T  F  N  N  Y  G  M  H  W  V  R  Q  A
                                        <----- CDR1 ----->

121  CCAGGCAAGGGGCTGGAGTGGGTGGCAGTTATATGGTATGATGGAAGTAATAAAAACTAT    180
     P  G  K  G  L  E  W  V  A  V  I  W  Y  D  G  S  N  K  N  Y
                                  <---------- CDR2 ----------

181  GCAGACTCCGTGAAGGGCCGATTCACCATCTCCAGAGACAACTCCAAGAACACGCTGTAT    240
     A  D  S  V  K  G  R  F  T  I  S  R  D  N  S  K  N  T  L  Y
     ------>

241  CTGCAAATGAACAGCCTGAGAGCCGAGGACACGGCTGTGTATTACTGTGCCGAGAGAACGT    300
     L  Q  M  N  S  L  R  A  E  D  T  A  V  Y  Y  C  A  R  E  R
                                                          <-----

301  ACTACGATGTCTGGAGTGATCATTCCTCGCCGGTATTTGACTACTGGGGCCAGGGAACC    360
     T  T  M  S  G  V  I  I  P  R  R  Y  F  D  Y  W  G  Q  G  T
     -------------- CDR3 -------------->

361  CG  ------PCR PRIMER------    378
```

FIG. 13

```
  1  ------PCR PRIMER------       GGGRGGCGTGGTCCAGCCTGGGAGGTCCCTGAGACTC      60
                                   G  G  V  V  Q  P  G  R  S  L  R  L

61  TCCTGTGCAGCCTCTGGATTCACCTTCAGTAGCTATGGCATGCACTGGGTCCGCCAGGCT      120
      S  C  A  A  S  G  F  T  F  S  S  Y  G  M  H  W  V  R  Q  A
                              <------ CDR1 ------>

121  CCAGGCAAGGGGCTGGAGTGGGTGGCAGTTATTTGGTATGATGGAAGTAATAAATACTAT      180
      P  G  K  G  L  E  W  V  A  V  I  W  Y  D  G  S  N  K  Y  Y
                                    <------------ CDR2

181  GCAGACTCCGTGAAGGGCCGATTCACCATCTCCAGAGACAATTCCAAGAACACGCTGTAT      240
      A  D  S  V  K  G  R  F  T  I  S  R  D  N  S  K  N  T  L  Y
      ------>

241  CTGCAAATGAACAGCCTGAGAGCCGAGGACACGGCTGTATATTACTGTGCGAGAGAAGTT      300
      L  Q  M  N  S  L  R  A  E  D  T  A  V  Y  Y  C  A  R  E  V
                                                            <------

301  ACTATGGTTCGGGGAGTTAGGCGTTACTACGGTATGGACGTCTGGGGCCCAGGGACCAC-  360
      T  M  V  R  G  V  R  R  Y  Y  G  M  D  V  W  G  P  G  T
      ------------ CDR3 ------------>

361  ------PCR PRIMER------      375

FIG. 14
```

MONOCLONAL ANTIBODIES

This invention relates to novel monoclonal anti-RhD antibodies prepared by recombinant DNA methods.

The Rhesus blood group system is a major antigenic constituent of the human red blood cell membrane; of this group, the RhD antigen is of particular clinical importance in relation to isoimmune reactions. An Rh D-individual with anti-RhD who receives RhD+ blood is liable to suffer substantial red blood cell (RBC) destruction due to the RhD phenotype incompatibility, and thus blood of donors must routinely be classified as RhD+ or RhD-. Anti RhD monoclonal antibodies (anti-D Mabs) are capable of providing blood-typing reagents of high specificity and reliability.

The RhD antigen is also responsible for haemolytic disease of the newborn (HDN). This condition arises in newborn RhD+ infants of RhD- mothers previously sensitised to RhD Antigen as a result of IgG anti-RhD antibodies crossing the placenta during pregnancy and causing foetal red blood cell (RBC) destruction. Sensitization of the RhD- mother to RhD antigen often occurs during the birth of an earlier RhD+ child due to some foetal RBCs entering the maternal circulation and being recognised as foreign by the maternal immune system. To reduce the incidence of HDN, it is routine practice in the United Kingdom and many other countries to give anti-RhD antibodies to RhD- mothers immediately after the birth of an RhD+ infant so that any RhD+ RBCs which may have entered the maternal circulation are rapidly removed.

The search for the most effective anti D Mabs has proved to be extremely time consuming, involving the isolation of B-lymphocytes from humans immunised against RhD, usually Rh-ve mothers who have given birth to Rh+ve children. Such lymphocytes are subjected to EBV treatment to provide an immortalised cell-line directly or the EBV-treated cells are hybridised with suitable mouse myeloma cells to provide a hydridoma: The cell-line line or hybridoma may then be used to produce the anti-D Mab in the conventional way.

However, there are significant differences between anti-D Mabs in terms of their binding affinities for red cells, their ability to recognise D-variants such as $D''$ and $D^{VI}$, and their ability to destroy target cells by phagocytosis or cell-mediated lysis. It is desirable, therefore, to have available a method of combining the favourable parameters of different anti-D Mabs or, indeed of combining the most favourable features of selected anti-D Mabs with Mabs of quite different specificities which present particular advantages, in order to produce so-called chimaeric Mabs.

The concept of building chimaeric Mabs, has been described by Jones et al (Nature 321, 522–525 (1986)) and Riechmann et al (Nature 332, 323–327 (1988)). Three dimensional studies have shown that immunoglobulins comprise essentially constant regions common to most Mabs and terminally situated variable domains associated with antigen binding.

It has been shown that the variable domains consist of two β-sheets joined by a disulphide bridge with their hydrophobic faces in contact. Sequence comparisons among heavy- and light-chain variable domains ($V_H$ and $V_L$ respectively) have revealed that each of these domains comprises three hypervariable domains or complementarity determining regions (CDRs) set in a framework of four relatively conserved regions, the framework regions (FRs). The CDRs are primarily responsible for the recognition of specific antigens. The structure of the β-sheet framework is similar in different antibodies, as the packing together of $V_L$ and $V_H$ FRS is conserved and therefore the orientation of $V_L$ with respect to $V_H$ is fixed.

Genes coding for a number of Mabs are now available and the sequences coding for the variable regions $V_L$ and $V_H$ have been determined. It is thus possible to replace the latter sequences by DNA coding for $V_L$ and $V_H$ from different Mabs and indeed to construct the latter by incorporating DNA coding for chosen CDRs into DNA coding for a standard set of FRs. It is thus possible to construct genes coding for chimeric anti-D Mabs having the CDRs from anti-D Mabs possessing particularly desirable specificities or other properties and framework and constant regions derived from Mabs having other desirable properties.

It is a prerequisite of such construction that the amino acid sequences of the CDR regions of the chosen anti-D Mabs and/or the genes coding for them, should be known. The specific CDR gene sequences can then be synthesised, conveniently by chemical synthesis of the appropriate oligonucleotides, and incorporated into DNA sequences coding for a standard set of FRs and the human (or other) constant region. Of course, the FRs may be identical with those of the Mab providing the constant region or, more conveniently, they may be a standard set of FRs which can be used generally in the synthesis of chimeric Mabs.

We have produced a number of anti-D Mabs of particular interest and have determined their amino acid sequences, thus making it possible for DNA sequences corresponding to their CDRs to be synthesised and incorporated into $V_H$ and $V_L$ sequences as described above. These may then be combined with DNA coding for the constant region to enable novel anti-D Mabs to be synthesised which may have lower, the same or higher binding ability.

Thus, according to one aspect we provide DNA sequences comprising oligonucleotides encoding CDR1, CDR2, and CDR3 regions of $V_H$ (SEQ ID NOS:1–11, 12–22 and 23–34, respectively) and $V_L$ (SEQ ID NOS:35–37, 38–40 and 41–42, respectively) domains of antibodies against the human RhD antigen, and functional equivalents thereof. In particular, we have investigated and sequenced eleven Mabs, namely a) FOG-B, b) PAG-1, c) MAD-2, d) FOG-1, e) FOM-1, f) FOM-A, g) BRAD-3, h) JAC-10, i) GAD-2, J) REG-A, K) HAM-B, whose heavy and light chain sequences are represented in FIGS. 2–14, of the accompanying drawings, and which have both varied and particularly useful binding specificities. The FIGS. 2 and 3 show the nucleotide and amino acid sequences of the light chain variable domains of the Mabs FOG-B and PAG-1. Corresponding sequences for the heavy chain variable domains of these two Mabs are shown in FIGS. 4 and 5, and sequences of the heavy chain variable domains of the Mabs MAD-2, FOG-1, FOM-A, BRAD-3, JAC-10, GAD-2, REG-A and HAM-B are shown in FIGS. 6–14.

Synthetic genes, for both heavy and light chains may be created by combining selected CDR 1, 2, and 3 regions, which may be selected from different antibody molecules having varied binding specificities.

Thus according to a further aspect, we provide DNA molecules coding for the heavy or light chain fragments of a monoclonal antibody or fragment thereof comprising CDR1, CDR2 and CDR3 encoding oligonucleotides from antibodies FOG-B, PAG-1, MAD-2, FOG-1, FOM-1, FOM-A, BRAD-3, JAC-10, GAD-2, REG-A and HAM-B as illustrated in FIGS. 2–14.

In order to create functional genes, such oligonucleotides must be incorporated into a backbone sequence such that when expressed, functional proteins result.

Thus according to a further aspect, we provide DNA molecules comprising a gene coding for the framework regions of a human antibody light or heavy chain having inserted therein in the correct CDR region, oligonucleotides encoding CDR1, CDR2 and CDR3 regions according to the present invention.

In the synthesis of a chimeric Mab in accordance with the invention, single stranded DNA coding for the $V_H$ region of a chosen Mab (not necessarily an anti-D Mab) is incorporated in single stranded form into a vector capable of producing single stranded DNA, such as the M13 bacteriophage. FIG. 1 shows diagrammatically the structure of a single stranded $V_H$ DNA including framework regions FR1 to FR4 with complementarity determining regions CDR1 to CDR3 of a Mab. These steps can be accomplished by conventional techniques such as those described in Riechmann et al (Nature, 332, 323–327, (1988)).

Three oligonucleotides may then be prepared corresponding to the CDR regions of the chosen anti-D Mab variable domain, eg the $V_H$ region of FOG-B as shown in FIG. 4, and will include several nucleotides on either side of each CDR region to permit hybridisation with the framework regions FR1 to FR4 (see FIG. 1). The sequences of the latter will normally be substantially homologous with those of the anti-D Mab (e.g. FOG-B) but since the oligonucleotides will normally be synthesised chemically, hybridisation may be ensured by matching the overlapping nucleotides exactly to the FRs 1 to 4. It may also be beneficial to modify the oligonucleotides to express the CDRs more efficiently in the eventual host cells.

The three oligonucleotides, shown in FIG. 1 as oligo 1 to oligo 3, may then be annealed to a single stranded $V_H$ DNA in the M13 vector and used as primers to synthesise second strand DNA containing the anti-D $V_H$ CDR sequences. This may be achieved conventionally using a suitable polymerase. Since the antibody specificity is determined solely by the three CDR regions, the actual $V_H$ gene chosen for the framework template is immaterial. All that is required is that there is sufficient homology of the three chosen oligonucleotides with the template. This is ensured by appropriate design of the terminal nucleotides of the synthetic oligonucleotide primers. Thus the second strand may contain sequences from substantially any human antibody heavy chain gene, so long as the resulting expressed protein posesses the desired binding parameters.

The double stranded M13 vector may then be used to transform a suitable host microorganism e.g. a conventional *E. coli* and one or more clones selected which contain the required anti-D $V_H$ specificity. The correct clone may be identified by DNA seqencing.

The corresponding $V_L$ DNA (e.g. for FOG-B) may be prepared in the same way.

The DNA coding for the $V_H$ and $V_L$ regions may then be excised from the above vectors and introduced into other vectors.

According to a further aspect, we provide DNA molecules being synthetic genes for chimaeric antibody, heavy or light chains when incorporated into vectors capable of expressing such antibody chains. Preferred vectors include mammalian expression vectors, such as pSV2gpt (heavy chains) and pSV2neo (light chains) containing DNA coding for the human constant region. Such vectors are readily available from a number of laboratories, or can readily be prepared by incorporating DNA coding for human constant region into known mammalian vectors.

The expression vectors so constructed may then be co-transfected into an appropriate cell-line e.g. a non-secreting IgG myeloma, for large scale production.

Thus according to a yet further aspect, the present invention provides each of the CDR polypeptides of the Mabs FOG-B, PAG-1, MAD-2, FOG-1, FOM-1, FOM-A, BRAD-3, JAC-I0, GAD-2, REG-A and HAM-B shown in FIGS. 2–14 (SEQ ID NOS:43–55, respectively) of the accompanying drawings in single stranded or double stranded form in the absence of the constant and or framework regions of said Mabs.

According to a yet further aspect, the invention provides chimaeric antibody heavy and light chains of the variable domains comprising CDR polypeptide sequences of the present invention.

Knowledge of the antibody sequences according to the invention enables new chimaeric anti-D antibody molecules to be prepared, having appropriately designed binding specificities. These antibodies may be used for both therapy and diagnosis using presently known techniques.

According to a yet further aspect, we provide anti-RhD reagents comprising at least one antibody molecule according to the invention.

According to a still yet further aspect, we provide pharmaceutical compositions for use in passive immunisation to prevent haemolytic disease of the newborn comprising an antibody of the present invention together with at least one phamacologically acceptable carrier or diluent.

A sterile solution of such an antibody for human injection may be formulated in any physiologically acceptable aqueous medium, for example isotonic phosphate buffered saline or serum. Alternatively, the antibody may be supplied in a freeze-dried formulation ready for reconstitution prior to use.

EXAMPLE (1) Construction of Chimaeric Antibody Genes

Three oligonucleotide primers are synthesised using an Applied Biosystems machine according to the manufacturer's instructions and purified on an 8M Urea/polyacrylamide gel (Sanger & Coulson, Febs Lett., 87, 107–110, 1978). The primers are designed to comprise in their central regions sequences complementary to the CDR1, CDR2 and CDR3 regions of the anti-RhD antibody PAG-1 heavy chain gene, as identified according to the criteria described by Kabat et al. (Sequences of Proteins of Immunological Interest, U.S. Department of Health and Social Services, 1987).

The central sequences are flanked at both their 5' and 3' termini by sequences of 10 nucleotides which hybridise to the termini of the corresponding framework region sequences adjacent to the CDR sequence of the heavy chain antibody gene NEWM (Poljack et al., Biochemistry 16, 3412–3420, 1977). The primers are then hybridised to the derived NEWM single stranded DNA heavy chain sequence in the M13 bacteriophage and the complementary strand of the heavy chain variable region extended using DNA polymerase (Neuberger et al., Nature 314, 268–270 (1985), Jones et al., Nature 321, 522–5 (1986)). The M13 vector also contains an appropriate arrangement for ultimate expression, i.e. a leader sequence, and unique HindIII and BamHI restriction sites.

A similar construct is prepared from oligonucleotide primers homologous to the CDR regions of the PAG-1 anti-RhD antibody light chain genes, and utilising the M13 vector in which $V_L$ and $J_L$ regions of the antibody gene PAV1 (Sun et al., Nucleic Acids Research 13, 4921–4934, 1985) are cloned.

(2) Expression of Antibody Polypeptides

The cloned genes for the $V_H$ domains are excised using HindIII and BamHI and cloned into pSV2gpt (Mulligan and Berg, PNAS 78, 2072–6, 1981). The cloned light chain genes are similarly excised and cloned into pSV2neo (Southern and Berg, J. Molec. Appl. Genetics 1 327–381, 1981). Sequences encloding IgG1 constant regions are then inserted into the vectors (Riechmann et al., Nature 312, 323–7, (1988). Both vectors are then transfected by electroporation (Potter et al., PNAS 81, 7161–3, 1984) into the rat myeloma cell line YO (YB2/3.0 AG, 20) (Galfre and Milstein, Methods in Enzymology 73, 1–46, 1981) for antibody production.

---

SEQUENCE LISTING ( 1 ) GENERAL INFORMATION:

( i i i ) NUMBER OF SEQUENCES: 55

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AGTGGTGGTC TCTACTGGGG C                        21

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AGTTCCTACT GGAGC                            15

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GGTTACTACT GGAGC                            15

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GTTTACTACT GGACC                            15

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:5:

GGTTACTACT GGAAC                                                                      15

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GGTTACTACT GGAGC                                                                      15

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AGCTATGGCA TGCAC                                                                      15

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AGTTACTGGA TGCAC                                                                      15

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

AGCTATGGCA TGCAC                                                                      15

(2) INFORMATION FOR SEQ ID NO:10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AATTATGGCA TGCAC                                                                               15

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

AGCTATGGCA TGCAC                                                                               15

( 2 ) INFORMATION FOR SEQ ID NO:12:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

AGTATATTTT ATAGTGGGAG CACCTACTAC AATCCCTCCC TCAAGAGC                                           48

( 2 ) INFORMATION FOR SEQ ID NO:13:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

TATATCTATT ACAGTGGGAG CACCAACTAC AACCCCTCCC TCAGGAGT                                           48

( 2 ) INFORMATION FOR SEQ ID NO:14:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GAAATCAATC ATAGTGGAAG GACCAACTAC AACCCGTCCC TCAAGACT                                           48

( 2 ) INFORMATION FOR SEQ ID NO:15:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GAAATCAATC ATAGTGGAGG CGCCAACTAC AATCCGTCCC TCAAGAGT                                           48

( 2 ) INFORMATION FOR SEQ ID NO:16:

( i ) SEQUENCE CHARACTERISTICS:
            ( A ) LENGTH: 48 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:16:

GAAATCATTC ATAGTGGAAG CACCAACTAC AACCCGTCCC TCAAGAGT         48

( 2 ) INFORMATION FOR SEQ ID NO:17:

( i ) SEQUENCE CHARACTERISTICS:
            ( A ) LENGTH: 48 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:17:

GAAATCAGTC GTCGTGGAAG CACCAACTAC AACCCGTCCC TCAAGAGT         48

( 2 ) INFORMATION FOR SEQ ID NO:18:

( i ) SEQUENCE CHARACTERISTICS:
            ( A ) LENGTH: 51 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:18:

CTTATATGGT ATGATGGAAG TAATAAAGAA TATGCAGACT TCGTGAAGGG C      51

( 2 ) INFORMATION FOR SEQ ID NO:19:

( i ) SEQUENCE CHARACTERISTICS:
            ( A ) LENGTH: 51 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:19:

CGTATTAATA GTTATGGAAT TAGCACAAGT TACGCGAACT CCGTGAAGGG C      51

( 2 ) INFORMATION FOR SEQ ID NO:20:

( i ) SEQUENCE CHARACTERISTICS:
            ( A ) LENGTH: 51 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:20:

GTGATATGGT ATGATGGAAG TAATAAGTAC TATGCAGAGT CCGTGAAGGG C      51

( 2 ) INFORMATION FOR SEQ ID NO:21:

( i ) SEQUENCE CHARACTERISTICS:
            ( A ) LENGTH: 51 base pairs
            ( B ) TYPE: nucleic acid
            ( C ) STRANDEDNESS: single (D) TOPOLOGY: linear (i i) MOLECULE TYPE: DNA (genomic)

(x i) SEQUENCE DESCRIPTION: SEQ ID NO:21:

GTTATATGGT ATGATGGAAG TAATAAAAAC TATGCAGACT CCGTGAAGGG C    51

(2) INFORMATION FOR SEQ ID NO:22:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:22:

GTTATTTGGT ATGATGGAAG TAATAAATAC TATGCAGACT CCGTGAAGGG C    51

(2) INFORMATION FOR SEQ ID NO:23:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:23:

CCAGGCTATG GCGACACCTC GGTACGGAAG AGGGTTTGGA ATATGGACCT C    51

(2) INFORMATION FOR SEQ ID NO:24:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:24:

GTTTGGTTT CCCGTACCAT TTCACAGTAC TCCTATTACA TGGACGTC    48

(2) INFORMATION FOR SEQ ID NO:25:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:25:

GTTTGGTTT CCCGTACGAT TTCACAGTAC TCCTATTACA TGGACGTC    48

(2) INFORMATION FOR SEQ ID NO:26:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:26:

CTGTGGCTCG ATGGACATGG GTACAAGTTT GACTAC         36

( 2 ) INFORMATION FOR SEQ ID NO:27:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

GGCCGGTCCC GTTATAGTGG TTACGGCTTC TACTCCGGCA TGGACGTC         48

( 2 ) INFORMATION FOR SEQ ID NO:28:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

GGCTTAGAAC GTCCGATTAG GAACCAGCTG CTAAACCGTC TCGGTTACTA CATGGACGTC         60

( 2 ) INFORMATION FOR SEQ ID NO:29:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

GCCTTGGACT ACATCTCCTT GGATTACGGT ATGGACGTC         39

( 2 ) INFORMATION FOR SEQ ID NO:30:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

GATAGTCCCA AAATGAGGGC TGGAAGTATG TTTCGCTACT ACTACATGGA CGTC         54

( 2 ) INFORMATION FOR SEQ ID NO:31:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

GGAGAGCGCA TAGCAGCTCG TCTCTTGTCG GGCGGGTACG GTATGGACGT C         51

( 2 ) INFORMATION FOR SEQ ID NO:32:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:32:

GTCGTTAGCA GCAACCGGTA CTCTCTAAGC TACTATTATT ACTACATGGA CGTC      54

( 2 ) INFORMATION FOR SEQ ID NO:33:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:33:

GAACGTACTA CGATGTCTGG AGTGATCATT CCTCGCCGGT ATTTTGACTA C      51

( 2 ) INFORMATION FOR SEQ ID NO:34:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:34:

GAAGTTACTA TGGTTCGGGG AGTTAGGCGT TACTACGGTA TGGACGTC      48

( 2 ) INFORMATION FOR SEQ ID NO:35:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:35:

TCCGGAACCA GCTCCAACAT TGGGAATAAT TATGTATCC      39

( 2 ) INFORMATION FOR SEQ ID NO:36:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:36:

GGGGGAAACA ACATTGGGCG TAAAAGTGTG CAC      33

( 2 ) INFORMATION FOR SEQ ID NO:37:

( i ) SEQUENCE CHARACTERISTICS:
    ( A ) LENGTH: 33 base pairs
    ( B ) TYPE: nucleic acid
    ( C ) STRANDEDNESS: single (D) TOPOLOGY: linear (i i) MOLECULE TYPE: DNA (genomic)

(x i) SEQUENCE DESCRIPTION: SEQ ID NO:37:

GGGGGAAACA ACATTGGACG TAAAAGTGTG CAC 33

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:38:

GACAATAATA AGCGACCCTC A 21

(2) INFORMATION FOR SEQ ID NO:39:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:39:

GGTGCTAGCG AGCGGCCCTC A 21

(2) INFORMATION FOR SEQ ID NO:40:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:40:

GGTGCTAGCG ACCGGCCCTC A 21

(2) INFORMATION FOR SEQ ID NO:41:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:41:

GCAACATGGG ATAGCAGCCT GAGTGCTGTG GTG 33

(2) INFORMATION FOR SEQ ID NO:42:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:42:

CAGGTGTGGG ATAGTAGTAG TGCTCATCCG GGGGTGGTA 39

( 2 ) INFORMATION FOR SEQ ID NO:43:

( i ) SEQUENCE CHARACTERISTICS:
        ( A ) LENGTH: 333 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

CAGTCTGTGT TGACGCAGCC GCCCTGAGTG TCTGCGGCCC CAGGACAGAA GGTCACCATC 60
TCCTGCTCCG GAACCAGCTC CAACATTGGG AATAATTATG TATCCTGGTA TCAGCAGCTC 120
CCAGGAACAG CCCCCAAACT CCTCATTTAT GACAATAATA AGCGACCCTC AGGGATTCCT 180
GACCGATTCT CTGGCTCCAA GTCTGGCACG TCAGCCACCC TGGGCATCAC CGGACTCCGG 240
ACTGGGGACG AGGCCGATTA TTACTGCGCA ACATGGGATA GCAGCCTGAG TGCTGTGGTG 300
TTCGGCGGAG GGACCAAGCT GACCGTCCTA AGT 333

( 2 ) INFORMATION FOR SEQ ID NO:44:

( i ) SEQUENCE CHARACTERISTICS:
        ( A ) LENGTH: 333 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

TCCTATGTGC TGACTCAGCC ACCCTCGGTG TCAGTGGCCC CAGGACAGAC GGCCAGGATT 60
ACCTGTGGGG GAAACAACAT GGACGTAAA AGTGTGCACT GGTACCAGCA GAAGCCAGGC 120
CAGGCCCCTG TGCTGGTCGT CTATGGTGCT AGCGACCGGC CCTCAGGGAT CCCTGAGCGA 180
TTCTCTGGCT CCAACTCTGG GAACACGGCC ACCCTGACCA TCAGCAGGGT CGCAGCCGGG 240
GATGAGGCCG ACTATTACTG TCAGGTGTGG GATAGTAGTA GTGCTCATCC GGGGGTGGTA 300
TTCGGCGGAG GGACCAAGCT GACCGTCCTA GGT 333

( 2 ) INFORMATION FOR SEQ ID NO:45:

( i ) SEQUENCE CHARACTERISTICS:
        ( A ) LENGTH: 381 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

CAGCTGCGGC TGCAGGAGTC GGGCCCAGGA CTGGTGAAGC CTTCGGAGAC CCTGTCCCTC 60
ACCTGCAGTG TCTCTGGTGG CTCCGTCAGC AGTGGTGGTC TCTACTGGGG CTGGGTCCGC 120
CAGCCCCCAG GAAGGGGCT CGAATGGATT GGCAGTATAT TTTATAGTGG GAGCACCTAC 180
TACAATCCCT CCCTCAAGAG CCGAGTCACC ATATCCGTAG ACACGTTGAA GAATAACTTC 240
TCCCTGAAGC TGAGTTCTGT GACCGCCGCA GACACGGCTG TTTATTACTG TACGAGACCA 300
GGCTATGGCG ACACCTCGGT ACGGAAGAGG GTTTGGAATA TGGACCTCTG GGGCCAAGGG 360
ACCACGGTCA CCGTCTCCTC G 381

( 2 ) INFORMATION FOR SEQ ID NO:46:

( i ) SEQUENCE CHARACTERISTICS:
        ( A ) LENGTH: 372 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

```
CAGGTGCAGC  TGCAGGAGTC  GGGCCCAGGA  CTGGTGAAGC  CTTCGGAGAC  CCTGTCCGTC      60
ACCTGCACTG  TCTCTGGTGG  CTCCGTCAGT  AGTTCCTACT  GGAGCTGGAT  CCGGCAGCCC     120
CCAGGGAAGG  GACCGGAGTG  GATTGGGTAT  ATCTATTACA  GTGGGAGCAC  CAACTACAAC     180
CCCTCCCTCA  GGAGTCGAGT  CACCATATCA  GTAGACACGT  CCAAGAACCA  GTTCTCCCTG     240
AAGCTGGGCT  CTGTGACCGC  TGCGGACACG  GCCGTGTATT  ACTGTGCGAG  AGTTTTGGTT     300
TCCCGTACGA  TTTCACAGTA  CTCCTATTAC  ATGGACGTCT  GGGGCAAAGG  GACCACGGTC     360
ACCGTGTCCT  CA                                                             372
```

( 2 ) INFORMATION FOR SEQ ID NO:47:

( i ) SEQUENCE CHARACTERISTICS:
        ( A ) LENGTH: 321 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..321
        ( D ) OTHER INFORMATION: /note= "Nucleotides 1-321 corres.
            to nucleotides 24-344 of Fig. 6/14. Nucleotides
            1-23 and 345- 360 represent PCR primers."

( x i ) SEQUENCE DESCRIPTION: SEQ ID NO:47:

```
CGCAGGACTG  TTGAAGCCTT  CGGAGACCCT  GTCCCTCACC  TGCGCTGTCT  ATGGTGGGTC      60
CTTCAGTGGT  TACTACTGGA  GCTGGATCCG  CCAGCCTCCA  GGGAAGGGGC  TGGAGTGGAT     120
TGGGGAAATC  AATCATAGTG  GAAGGACCAA  CTACAACCCG  TCCCTCAAGA  CTCGAGTCAC     180
CATATCAGTA  GACACGTCCA  AGAACCAGTT  CTCCCTGAAG  CTGAGTTCTG  TGACCGCCGC     240
GGACACGGCT  GTGTATTACT  GTGCGAGACT  GTGGCTCGAT  GGACATGGGT  ACAAGTTTGA     300
CTACTGGGGC  CAGGGAACCC  T                                                  321
```

( 2 ) INFORMATION FOR SEQ ID NO:48:

( i ) SEQUENCE CHARACTERISTICS:
        ( A ) LENGTH: 372 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

```
CAGGTGCATC  TACAGCAGTG  GGGCACAGGG  CTGTTGAAGC  CTTCGGAGAC  CCTGTCCCTC      60
ACCTGCGCTG  TCCATGGTGG  GTCCTTCAAT  GTTTACTACT  GGACCTGGAT  CCGCCAGCCC     120
CCAGGAAAGG  CGCTGGAGTG  GATTGGGGAA  ATCAATCATA  GTGGAGGCGC  CAACTACAAT     180
CCGTCCCTCA  AGAGTCGAGT  CACCATGTCA  GCAGACACGT  CCAAGAACCA  GTTCTCCCTG     240
```

| A A A C T G A C C T | C T G T G A C C G C | C G C G G A C A C G | G C T G T G T T T T | A T T G T G C G A G | A G G C C G G T C C | 3 0 0 |
| C G T T A T A G T G | G T T A C G G C T T | C T A C T C C G G C | A T G G A C G T C T | G G G G C C C A G G | G A C C A C G G T C | 3 6 0 |
| A C C G T C T C C T | C A | | | | | 3 7 2 |

( 2 ) INFORMATION FOR SEQ ID NO:49:

( i ) SEQUENCE CHARACTERISTICS:
        ( A ) LENGTH: 384 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

| C A G G T G C A G C | T A C A G C A G T G | G G G C G C A G G A | C T G T T G A A G C | C T T C G G A G A C | C C T G T C C C T C | 6 0 |
| A C C T G C G C T G | T C T A T G G T G G | G T C C T T C A G T | G G T T A C T A C T | G G A A C T G G A T | C C G C C A G C C C | 1 2 0 |
| C C A G G G A A G G | G G C T G G A G T G | G A T T G G G G A A | A T C A T T C A T A | G T G G A A G C A C | C A A C T A C A A C | 1 8 0 |
| C C G T C C C T C A | A G A G T C G A G T | C A C C A T G T C A | G T A G A C A C G T | C C A A G A A C C A | G T T C T C C C T G | 2 4 0 |
| A A G C T G A G C T | C T G T G A C C G C | C G C G G A C A C G | G C T G T G T A T T | A C T G T G C G A G | A G G C T T A G A A | 3 0 0 |
| C G T C C G A T T A | G G A A C C A G C T | G C T A A A C C G T | C T C G G T T A C T | A C A T G G A C G T | C T G G G G C A A A | 3 6 0 |
| G G G A C C A C G G | T C A C C G T C T C | C T C A | | | | 3 8 4 |

( 2 ) INFORMATION FOR SEQ ID NO:50:

( i ) SEQUENCE CHARACTERISTICS:
        ( A ) LENGTH: 363 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

| C A G G T G C A G C | T A C A G C A G T G | G G G C G C A G G A | C T G T T G A A G C | C T T C G G A G A C | C C T G T C C C T C | 6 0 |
| A C C T G C G C T G | T C T A T G G T G G | G T C C T T C A G T | G G T T A C T A C T | G G A G C T G G A T | C C G C C A G C C C | 1 2 0 |
| C C A G G G A A G G | G G C T G G A G T G | G A T T G G G G A A | A T C A G T C G T C | G T G G A A G C A C | C A A C T A C A A C | 1 8 0 |
| C C G T C C C T C A | A G A G T C G A G T | C G C C A T A T C A | G T A G A C A C G T | C C A A G A A C C A | G T T C T C C C T G | 2 4 0 |
| A A G G T G A G G T | C T G T G A C C G C | C G C G G A C A C G | G C T G T G T A T T | A C T G T G C G A G | A G C C T T G G A C | 3 0 0 |
| T A C A T C T C C T | T G G A T T A C G G | T A T G G A C G T C | T G G G G C C A A G | G G A C C A C G G T | C A C C G T C T C C | 3 6 0 |
| T C A | | | | | | 3 6 3 |

( 2 ) INFORMATION FOR SEQ ID NO:51:

( i ) SEQUENCE CHARACTERISTICS:
        ( A ) LENGTH: 342 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..342
        ( D ) OTHER INFORMATION: /note= "Nucleotides 1-381 corres.
            to nucleotides 24-365 of Fig. 10/14. Nucleotides
            1-23 and 366- 381 represent PCR primers."

( x i ) SEQUENCE DESCRIPTION: SEQ ID NO:51:

```
GGGAGGCGTG   GTCCAGCCTG   GGAGGTTCCT   GAGACTCTCC   TGTGCAGCGT   CTGGATTCAC        60

CTTCAGTAGC   TATGGCATGC   ACTGGGTCCG   CCAGGCTCCA   GGCAAGGGGC   TGGAGTGGGT       120

GGCACTTATA   TGGTATGATG   GAAGTAATAA   AGAATATGCA   GACTTCGTGA   AGGGCCGATT       180

CACCATCTCC   AGAGACAATT   CCAAGAATAC   ACTGTATCTG   CAAATGAACA   GCCTGAGAGC       240

CGAGGACACG   GCTGTGTATT   ACTGTGCGAC   AGATAGTCCC   AAAATGAGGG   CTGGAAGTAT       300

GTTTCGCTAC   TACTACATGG   ACGTCTGGGG   CAAAGGGACC   AC                            342
```

( 2 ) INFORMATION FOR SEQ ID NO:52:

( i ) SEQUENCE CHARACTERISTICS:
    ( A ) LENGTH: 339 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..339
    ( D ) OTHER INFORMATION: /note= "Nucleotides 1-378 corres.
      to nucleotides 24-362 of Fig. 11/14. Nucleotides
      1-23 and 363- 378 represent PCR primers."

( x i ) SEQUENCE DESCRIPTION: SEQ ID NO:52:

```
GGGAGGCTTA   GTTCAGCCTG   GGGGGTCCCT   GAGACTCTCC   TGTGCAGCCT   CTGGATTCAC        60

CTTCAGTAGT   TACTGGATGC   ACTGGGTCCG   CCAAGCTCCA   GGGAAGGGGC   TGGTGTGGGT       120

CTCACGTATT   AATAGTTATG   GAATTAGCAC   AAGTTACGCG   AACTCCGTGA   AGGGCCGATT       180

CACCATCTCC   AGAGACAACG   CCAAGAACAC   GCTGTATCTG   CAAATGAACA   CTCTGAGAGC       240

CGAGGACACG   GCTGTGTATT   ACTGTGCAAG   AGGAGAGCGC   ATAGCAGCTC   GTCTCTTGTC       300

GGGCGGGTAC   GGTATGGACG   TCTGGGGCCA   AGGGACCAC                                  339
```

( 2 ) INFORMATION FOR SEQ ID NO:53:

( i ) SEQUENCE CHARACTERISTICS:
    ( A ) LENGTH: 342 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..342
    ( D ) OTHER INFORMATION: /note= "Nucleotides 1-381 corres.
      to nucleotides 24-365 of Fig. 12/14. Nucleotides
      1-23 and 366- 381 represent PCR primers."

( x i ) SEQUENCE DESCRIPTION: SEQ ID NO:53:

```
GGGAGGCGTG   GTCCAGCCTG   GGAGGTCCCT   GAGACTCTCC   TGTGCAGCGT   CTGGATTCAC        60

CTTTAGTAGC   TATGGCATGC   ACTGGGTCCG   CCAGGCTCCA   GGCAAGGGGC   TGGAGTGGGT       120

GGCAGTGATA   TGGTATGATG   GAAGTAATAA   GTACTATGCA   GAGTCCGTGA   AGGGCCGATT       180

CACCATCTCC   AGAGACAATT   CCAAGAACAC   GCTGTATCTG   CAAATGAACA   GCCTGAGAGC       240

CGAGGACACG   GCTGTGTATT   ACTGTGCGAG   AGTCGTTAGC   AGCAACGGT   ACTCTCTAAG        300

CTACTATTAT   TACTACATGG   ACGTCTGGGG   CAAAGGGACC   AC                            342
```

( 2 ) INFORMATION FOR SEQ ID NO:54:

( i ) SEQUENCE CHARACTERISTICS:

-continued (A) LENGTH: 339 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..339
(D) OTHER INFORMATION: /note= "Nucleotides 1-378 corres. to nucleotides 24-362 of Fig. 13/14. Nucleotides 1-23 and 363- 378 represent PCR primers."

(xi) SEQUENCE DESCRIPTION: SEQ ID NO:54:

| | | | | | | |
|---|---|---|---|---|---|---|
| GGGAGGCGTG | GTCCAGCCTG | GGAGGTCCCT | GAGACTCTCC | TGTGCAGCGT | CTGGATTCAC | 60 |
| CTTCAATAAT | TATGGCATGC | ACTGGGTCCG | CCAGGCTCCA | GGCAAGGGGC | TGGAGTGGGT | 120 |
| GGCAGTTATA | TGGTATGATG | GAAGTAATAA | AAACTATGCA | GACTCCGTGA | AGGGCCGATT | 180 |
| CACCATCTCC | AGAGACAATT | CCAAGAACAC | GCTGTATCTG | CAAATGAACA | GCCTGAGAGC | 240 |
| CGAGGACACG | GCTGTGTATT | ACTGTGCGAG | AGAACGTACT | ACGATGTCTG | GAGTGATCAT | 300 |
| TCCTCGCCGG | TATTTTGACT | ACTGGGGCCA | GGGAACCCG | | | 339 |

(2) INFORMATION FOR SEQ ID NO:55:

(i) SEQUENCE CHARACTERISTICS:
(A) LENGTH: 335 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..335
(D) OTHER INFORMATION: /note= "Nucleotides 1-375 corres. to nucleotides 24-359 of Fig. 14/14. Nucleotides 1-23 and 360- 375 represent PCR primers."

(xi) SEQUENCE DESCRIPTION: SEQ ID NO:55:

| | | | | | | |
|---|---|---|---|---|---|---|
| GGGGGCGTGG | TCCAGCCTGG | GAGGTCCCTG | AGACTCTCCT | GTGCAGCGTC | TGGATTCACC | 60 |
| TTCAGTAGCT | ATGGCATGCA | CTGGGTCCGC | CAGGCTCCAG | GCAAGGGGCT | GGAGTGGGTG | 120 |
| GCAGTTATTT | GGTATGATGG | AAGTAATAAA | TACTATGCAG | ACTCCGTGAA | GGGCCGATTC | 180 |
| ACCATCTCCA | GAGACAATTC | CAAGAACACG | CTGTATCTGC | AAATGAACAG | CCTGAGAGCC | 240 |
| GAGGACACGG | CTGTGTATTA | CTGTGCGAGA | GAAGTTACTA | TGGTTCGGGG | AGTTAGGCGT | 300 |
| TACTACGGTA | TGGACGTCTG | GGGCCAGGG | ACCAC | | | 335 |

I claim:

1. An isolated, synthetic or recombinant DNA molecule comprising a nucleotide sequence encoding a $V_H$ domain of an antibody against the human RhD antigen, said $V_H$ domain comprising a CDR1, CDR2 and a CDR3 region, wherein said $V_H$ domain is selected from the group consisting of:
    (i) a $V_H$ domain comprising a CDR1 region encoded by the DNA sequence of AGTGGTGGTCTC-TACTGGGGC; a CDR2 region encoded by the DNA sequence of AGTATATTTTATAGTGGGAGCAC-CTACTACAATCCCTC CCTCAAGAGC; and a CDR3 region encoded by the DNA sequence of CCAG-GCTATGGCGACACCTCGGTACGGAA-GAGGGTTTGGAATATGGACCTC;
    (ii) a $V_H$ domain comprising a CDR1 region encoded by the DNA sequence of AGTTCCTACTGGAGC; a CDR2 region encoded by the DNA sequence of TATATCTATTACAGTGGGAGCACCAAC-TACAACCCCTCCCTC AGGAGT; and a CDR3 region encoded by the DNA sequence of GTTTTG-GTTTCCCGTACGATTTCACAGTACTC-CTATTACATGGACGTC;
    (iii) a $V_H$ domain comprising a CDR1 region encoded by the DNA sequence of GTTTACTACTGGACC; a CDR2 region encoded by the DNA sequence of GAAATCAATCATAGTGGAGGCGCCAAC-TACAATCCGTCC CTCAAGAGT; and a CDR3 region encoded by the DNA sequence of GGCCGGTC-CCGTTATAGTGGTTACGGCTTCTACTC-CGGCATGGACGTC;
    (iv) a $V_H$ domain comprising a CDR1 region encoded by the DNA sequence of GGTTACTACTGGAGC; a CDR2 region encoded by the DNA sequence of GAAATCAGTCGTCGTGGAAGCACCAAC-TACAACCCGTCCCTC AAGAGT; and a CDR3 region encoded by the DNA sequence of GCCTTG-GACTACATCTCCTTGGATTACGGTATGGACGTC;

(v) a $V_H$ domain comprising a CDR1 region encoded by the DNA sequence of AGCTATGGCATGCAC; a CDR2 region encoded by the DNA sequence of CTTATATGGTATGATGGAAGTAATAAA-GAATATGCAGACTTC GTGAAGGGC; and a CDR3 region encoded by the DNA sequence of GATAGTC-CCAAAATGAGGGCTGGAAGTAT-GTTTCGCTACTACTACATGGACGTC;

(vi) a $V_H$ domain comprising a CDR1 region encoded by the DNA sequence of AGTTACTGGATGCAC; a CDR2 region encoded by the DNA sequence of CGTATTAATAGTTATGGAATTAGCA-CAAGTTACGCGAACTCC GTGAAGGGC; and a CDR3 region encoded by the DNA sequence of GGAGAGCGCATAGCAGCTCGTCTCT-TGTCGGGCGGGTACGGTATGGACGTC;

(vii) a $V_H$ domain comprising a CDR1 region encoded by the DNA sequence of AGCTATGGCATGCAC; a CDR2 region encoded by the DNA sequence of GTGATATGGTATGATGGAAGTAATAAG-TACTATGCAGAGTCC GTGAAGGGC; and a CDR3 region encoded by the DNA sequence of GTCGTTAG-CAGCAACCGGTACTCTCTAAGCTACTAT-TATTACTACATGGACGTC;

(viii) a $V_H$ domain comprising a CDR1 region encoded by the DNA sequence of AATTATGGCATGCAC; a CDR2 region encoded by the DNA sequence of GTTATATGGTATGATGGAAG-TAATAAAAACTATGCAGACTCC GTGAAGGGC; and a CDR3 region encoded by the DNA sequence of GAACGTACTACGATGTCTGGAGTGAT-CATTCCTCGCCGGTATTTTGACTAC; and (ix) a $V_H$ domain comprising a CDR1 region encoded by the DNA sequence of AGCTATGGCATGCAC; a CDR2 region encoded by the DNA sequence of GTTATTTGGTATGATGGAAG-TAATAAATACTATGCAGACTCC GTGAAGGGC; and a CDR3 region encoded by the DNA sequence of GAAGTTACTATGGTTCGGGGAGTTAGGCGTT-ACTACGGTATGGACGTC, or a DNA molecule wherein at least one of said sequences has extended terminal regions.

2. A DNA molecule according to claim 1, wherein said $V_H$ domain comprises a CDR1 region encoded by the DNA sequence of AGTGGTGGTCTCTACTGGGGC; a CDR2 region encoded by the DNA sequence of AGTATATTTTAT-AGTGGGAGCACCTACTACAATCCCTC CCTCAA-GAGC; and a CDR3 region encoded by the DNA sequence of CCAGGCTATGGCGACACCTCGGTACG-GAAGAGGGTTTGGAATATGGACCTC.

3. A DNA molecule according to claim 1, wherein said $V_H$ domain comprises a $V_H$ domain comprising a CDR1 region encoded by the DNA sequence of AGTTCCTACTGGAGC; a CDR2 region encoded by the DNA sequence of TATATC-TATTACAGTGGGAGCACCAACTACAAC-CCCTCCCTC AGGAGT; and a CDR3 region encoded by the DNA sequence of GTTTTGGTTTCCCGTAC-GATTTCACAGTACTCCTATTACATGGACGTC.

4. A DNA molecule according to claim 1, wherein said $V_H$ domain comprises a CDR1 region encoded by the DNA sequence of GTTTACTACTGGACC; a CDR2 region encoded by the DNA sequence of GAAATCAATCAT-AGTGGAGGCGCCAACTACAATCCGTCC CTCAA-GAGT; and a CDR3 region encoded by the DNA sequence of GGCCGGTCCCGTTATAGTGGTTACGGCT-TCTACTCCGGCATGGACGTC.

5. A DNA molecule according to claim 1, wherein said $V_H$ domain comprises a CDR1 region encoded by the DNA sequence of GGTTACTACTGGAGC; a CDR2 region encoded by the DNA sequence of GAAAT-CAGTCGTCGTGGAAGCACCAACTACAAC-CCGTCCCTCAAGAGT; and a CDR3 region encoded by the DNA sequence of GCCTTGGACTACATCTCCTTG-GATTACGGTATGGACGTC.

6. A DNA molecule according to claim 1, wherein said $V_H$ domain comprises a CDR1 region encoded by the DNA sequence of AGCTATGGCATGCAC; a CDR2 region encoded by the DNA sequence of CTTATATGGTATGATG-GAAGTAATAAAGAATATGCAGACTTC GTGAAGGGC; and a CDR3 region encoded by the DNA sequence of GATAGTCCCAAAATGAGGGCTGGAAG-TATGTTTCGCTACTACTACATGGACGTC.

7. A DNA molecule according to claim 1, wherein said $V_H$ domain comprises a CDR1 region encoded by the DNA sequence of AGTTACTGGATGCAC; a CDR2 region encoded by the DNA sequence of CGTATTAATAGTTATG-GAATTAGCACAAGTTACGCGAACTCC GTGAAGGGC; and a CDR3 region encoded by the DNA sequence of GGAGAGCGCATAGCAGCTCGTCTCT-TGTCGGGCGGGTACGGTATGGACGTC.

8. A DNA molecule according to claim 1, wherein said $V_H$ domain comprises a CDR1 region encoded by the DNA sequence of AGCTATGGCATGCAC; a CDR2 region encoded by the DNA sequence of GTGATATGGTATGATG-GAAGTAATAAGTACTATGCAGAGTCC GTGAAGGGC; and a CDR3 region encoded by the DNA sequence of GTCGTTAGCAGCAACCGG-TACTCTCTAAGCTACTATTATTACTACATGGACGTC.

9. A DNA molecule according to claim 1, wherein said $V_H$ domain comprises a CDR1 region encoded by the DNA sequence of AATTATGGCATGCAC; a CDR2 region encoded by the DNA sequence of GTTATATGGTATGATG-GAAGTAATAAAAACTATGCAGACTCC GTGAAGGGC; and a CDR3 region encoded by the DNA sequence of GAACGTACTACGATGTCTGGAGTGAT-CATTCCTCGCCGGTATTTTGACTAC.

10. A DNA molecule according to claim 1, wherein said $V_H$ domain comprises a CDR1 region encoded by the DNA sequence of AGCTATGGCATGCAC; a CDR2 region encoded by the DNA sequence of GTTATTTGGTATGATG-GAAGTAATAAATACTATGCAGACTCC GTGAAGGGC; and a CDR3 region encoded by the DNA sequence of GAAGTTACTATGGTTCGGGGAGTTAG-GCGTTACTACGGTATGGACGTC.

11. The DNA molecule according to claim 1, further comprising a nucleotide sequence encoding a $V_L$ domain of the antibody comprising a CDR1, CDR2 and a CDR3 region, wherein said $V_L$ domain is selected from the group consisting of:

(i) a $V_L$ domain comprising a CDR1 region encoded by the DNA sequence TCCGGAACCAGCTCCAACAT-TGGGAATAATTATGTATCC; a CDR2 region encoded by the DNA sequence GACAATAATAAGC-GACCC TCA; and a CDR3 region encoded by the DNA sequence GCAACATGGGATAGCAGCCT-GAGTGCTGTGGTG; and (ii) a $V_L$ domain comprising a CDR1 region encoded by the DNA sequence GGGGGAAACAACATTGGACG- TAAAAGTGTGCAC; a CDR2 region encoded by the DNA sequence GGTGCTAGCGACCGGCCCTCA; and a CDR3 region encoded by the DNA sequence CAGGTGTGGGATAGTAGT AGTGCTCATCCGGGGGTGGTA.

12. An isolated, synthetic or recombinant DNA molecule comprising a nucleotide sequence encoding a $V_L$ domain of an antibody against the human RhD antigen, said $V_L$ domain comprising a CDR1, CDR2 and a CDR3 region, wherein said $V_L$ domain is selected from the group consisting of:

(i) a $V_L$ domain comprising a CDR1 region encoded by the DNA sequence TCCGGAACCAGCTCCAACATTGGGAATAATTATGTATCC; a CDR2 region encoded by the DNA sequence GACAATAATAAGCGACCC TCA; and a CDR3 region encoded by the DNA sequence GCAACATGGGATAGCAGCCTGAGTGCTGTGGTG; and (ii) a $V_L$ domain comprising a CDR1 region encoded by the DNA sequence GGGGGAAACAACATTGGACGTAAAAGTGTGCAC; a CDR2 region encoded by the DNA sequence GGTGCTAGCGACCGGCCCTCA; and a CDR3 region encoded by the DNA sequence C A G G T G T G G G A T A G T A G T AGTGCTCATCCGGGGGTGGTA, or a DNA molecule wherein at least one of said sequences has extended terminal regions.

13. The DNA molecule according to claim 12, wherein said $V_L$ domain comprises a CDR1 region encoded by the DNA sequence TCCGGAACCAGCTCCAACATTGGGAATAATTATGTATCC; a CDR2 region encoded by the DNA sequence GACAATAATAAGCGACCC TCA; and a CDR3 region encoded by the DNA sequence GCAACATGGGATAGCAGCCTGAGTGCTGTGGTG.

14. The DNA molecule according to claim 12, wherein said $V_L$ domain comprises a CDR1 region encoded by the DNA sequence GGGGGAAACAACATTGGACGTAAAAGTGTGCAC; a CDR2 region encoded by the DNA sequence GGTGCTAGCGACCGGCCCTCA; and a CDR3 region encoded by the DNA sequence CAGGTGTGGGATAGTAGTAGTGCTCAT CCGGGGGTGGTA.

15. The DNA molecule according to claim 12, further comprising a nucleotide sequence encoding a $V_H$ domain comprising a CDR1, CDR2 and a CDR3 region, wherein said $V_H$ domain is selected from the group consisting of:

(i) a $V_H$ domain comprising a CDR1 region encoded by the DNA sequence of AGTGGTGGTCTCTACTGGGGC; a CDR2 region encoded by the DNA sequence of AGTATATTTTATAGTGGGAGCACCTACTACAATCCCTC CCTCAAGAGC; and a CDR3 region encoded by the DNA sequence of CCAGGCTATGGCGACACCTCGGTACGGAAGAGGGTTTGGAATATGGACCTC;

(ii) a $V_H$ domain comprising a CDR1 region encoded by the DNA sequence of AGTTCCTACTGGAGC; a CDR2 region encoded by the DNA sequence of TATATCTATTACAGTGGGAGCACCAACTACAACCCCTCCCTC AGGAGT; and a CDR3 region encoded by the DNA sequence of GTTTTGGTTTCCCGTACGATTTCACAGTACTCCTATTACATGGACGTC;

(iii) a $V_H$ domain comprising a CDR1 region encoded by the DNA sequence of GTTTACTACTGGACC; a CDR2 region encoded by the DNA sequence of GAAATCAATCATAGTGGAGGCGCCAACTACAATCCGTCC CTCAAGAGT; and a CDR3 region encoded by the DNA sequence of GGCCGGTCCCGTTATAGTGGTTACGGCTTCTACTCCGGCATGGACGTC;

(iv) a $V_H$ domain comprising a CDR1 region encoded by the DNA sequence of GGTTACTACTGGAGC; a CDR2 region encoded by the DNA sequence of GAAATCAGTCGTCGTGGAAGCACCAACTACAACCCGTCCCTC AAGAGT; and a CDR3 region encoded by the DNA sequence of GCCTTGGACTACATCTCCTTGGATTACGGTATGGACGTC;

(v) a $V_H$ domain comprising a CDR1 region encoded by the DNA sequence of AGCTATGGCATGCAC; a CDR2 region encoded by the DNA sequence of CTTATATGGTATGATGGAAGTAATAAAGAATATGCAGACTTC GTGAAGGGC; and a CDR3 region encoded by the DNA sequence of GATAGTCC C A A A A T G A G G G C T G G A A G T A T GTTTCGCTACTACTACATGGACGTC;

(vi) a $V_H$ domain comprising a CDR1 region encoded by the DNA sequence of AGTTACTGGATGCAC; a CDR2 region encoded by the DNA sequence of C G TATTA ATA G TTAT G G A ATTA G C A CAAGTTACGCGAACTCC GTGAAGGGC; and a CDR3 region encoded by the DNA sequence of GGAGAGCGCATAGCAGCTCGTCTCTTGTCGGGCGGGTACGGTATGGACGTC;

(vii) a $V_H$ domain comprising a CDR1 region encoded by the DNA sequence of AGCTATGGCATGCAC; a CDR2 region encoded by the DNA sequence of GTGATATGGTATGATGGAAGTAATAAGTACTATGCAGAGTCC GTGAAGGGC; and a CDR3 region encoded by the DNA sequence of GTCGTTAGCAGCAACCGGTACTCTCTAAGCTACTATTATTACTACATGGACGTC;

(viii) a $V_H$ domain comprising a CDR1 region encoded by the DNA sequence of AATTATGGCATGCAC; a CDR2 region encoded by the DNA sequence of G T TATAT G G TAT G AT G G A A G TAATAAAAACTATGCAGACTCC GTGAAGGGC; and a CDR3 region encoded by the DNA sequence of GAACGTACTACGATGTCTGGAGTGATCATTCCTCGCCGGTATTTTGACTAC; and (ix) a $V_H$ domain comprising a CDR1 region encoded by the DNA sequence of AGCTATGGCATGCAC; a CDR2 region encoded by the DNA sequence of G T TAT T T G G TAT G AT G G A A G TAATAAATACTATGCAGACTCC GTGAAGGGC; and a CDR3 region encoded by the DNA sequence of GAAGTTACTATGGTTCGGGGAGTTAGGCGTTACTACGGTATGGACGTC.

16. An isolated, synthetic or recombinant DNA molecule encoding a gene which codes for the framework region of a human antibody heavy chain having inserted therein a CDR1, CDR2 and a CDR3 region, wherein the combination of said CDR1, CDR2 and CDR3 regions is selected from the group consisting of:

(i) a CDR1 region encoded by the DNA sequence of AGTGGTGGTCTCTACTGGGGC; a CDR2 region encoded by the DNA sequence of AGTATATTTTATAGTGGGAGCACCTACTACAATCCCTC CCTCAAGAGC; and a CDR3 region encoded by the DNA sequence of CCAGGCTATGGCGACACCTCGGTACGGAAGAGGGTTTGGAATATGGACCTC;

(ii) a CDR1 region encoded by the DNA sequence of AGTTCCTACTGGAGC; a CDR2 region encoded by the DNA sequence of TATATCTATTACAGTGGGAGCACCAACTACAACCCCTCCCTC AGGAGT; and a CDR3 region encoded by the DNA sequence of GTTTTGGTTTCCCGTACGATTTCACAGTACTCCTATTACATGGACGTC;

(iii) a CDR1 region encoded by the DNA sequence of GTTTACTACTGGACC; a CDR2 region encoded by the DNA sequence of GAAATCAATCATAGTGGAGGCGCCAACTACAATCCGTCC CTCAAGAGT; and a CDR3 region encoded by the DNA sequence of GGCCGGTCCCGTTATAGTGGTTACGGCTTCTACTCCGGCATGGACGTC;

(iv) a CDR1 region encoded by the DNA sequence of GGTTACTACTGGAGC; a CDR2 region encoded by the DNA sequence of GAAATCAGTCGTCGTGGAAGCACCAACTACAACCCGTCCCTCAAGAGT; and a CDR3 region encoded by the DNA sequence of GCCTTGGACTACATCTCCTTGGATTACGGTATGGACGTC;

(v) a CDR1 region encoded by the DNA sequence of AGCTATGGCATGCAC; a CDR2 region encoded by the DNA sequence of CTTATATGGTATGATGGAAGTAATAAAGAATATGCAGACTTC GTGAAGGGC; and a CDR3 region encoded by the DNA sequence of GATAGTCCCAAAATGAGGGCTGGAAGTATGTTTCGCTACTACTACATGGACGTC;

(vi) a CDR1 region encoded by the DNA sequence of AGTTACTGGATGCAC; a CDR2 region encoded by the DNA sequence of CGTATTAATAGTTATGGAATTAGCACAAGTTACGCGAACTCC GTGAAGGGC; and a CDR3 region encoded by the DNA sequence of GGAGAGCGCATAGCAGCTCGTCTCTTGTCGGGCGGGTACGGTATGGACGTC;

(vii) a CDR1 region encoded by the DNA sequence of AGCTATGGCATGCAC; a CDR2 region encoded by the DNA sequence of GTGATATGGTATGATGGAAGTAATAAGTACTATGCAGAGTCC GTGAAGGGC; and a CDR3 region encoded by the DNA sequence of GTCGTTAGCAGCAACCGGTACTCTCTAAGCTACTATTATTACTACATGGACGTC;

(viii) a CDR1 region encoded by the DNA sequence of AATTATGGCATGCAC; a CDR2 region encoded by the DNA sequence of GTTATATGGTATGATGGAAGTAATAAAAACTATGCAGACTCC GTGAAGGGC; and a CDR3 region encoded by the DNA sequence of GAACGTACTACGATGTCTGGAGTGATCATTCCTCGCCGGTATTTTGACTAC; and (ix) a CDR1 region encoded by the DNA sequence of AGCTATGGCATGCAC; a CDR2 region encoded by the DNA sequence of GTTATTTGGTATGATGGAAGTAATAAATACTATGCAGACTCC GTGAAGGGC; and a CDR3 region encoded by the DNA sequence of GAAGTTACTATGGTTCGGGGAGTTAGGCGTTACTACGGTATGGACGTC, or a DNA molecule wherein at least one of said sequences has extended terminal regions.

17. An isolated, synthetic or recombinant DNA molecule encoding a gene which codes for the framework region of a human antibody light chain having inserted therein a CDR1, CDR2 and a CDR3 region, wherein the combination of said CDR1, CDR2 and CDR3 regions is selected from the group consisting of:

(i) a CDR1 region encoded by the DNA sequence TCCGGAACCAGCTCCAACATTGGGAATAATTATGTATCC; a CDR2 region encoded by the DNA sequence GACAATAATAAGCGACCC TCA; and a CDR3 region encoded by the DNA sequence GCAACATGGGATAGCAGCCTGAGTGCTGTGGTG; and (ii) a CDR1 region encoded by the DNA sequence GGGGGAAACAACATTGGACGTAAAAGTGTGCAC; a CDR2 region encoded by the DNA sequence GGTGCTAGCGACCGGCCCTCA; and a CDR3 region encoded by the DNA sequence CAGGTGTGGGATAGTAGT AGTGCTCATCCGGGGGTGGTA, or a DNA molecule wherein at least one of said sequences has extended terminal regions.

18. A vector comprising the DNA molecule of claim 16 operably linked in proper reading frame to sequences which direct the expression of the $V_H$ domain encoded by said DNA molecule.

19. The vector of claim 18, wherein said vector is a pSV2gpt vector.

20. The vector of claim 18, wherein said vector is replicable in mammalian cells.

21. A vector comprising the DNA molecule of claim 12 operably linked in proper reading frame to sequences which direct the expression of the $V_L$ domain encoded by said DNA molecule.

22. The vector of claim 21, wherein said vector is a pSV2neo vector.

23. The vector of claim 21, wherein said vector is replicable in mammalian cells.

* * * * *

UNITED STATES PATENT AND TRADEMARK OFFICE
CERTIFICATE OF CORRECTION

PATENT NO. : 5,831,063

DATED: : November 3, 1998

INVENTOR(S) : Nevin Campbell HUGHES-JONES

It is certified that error appears in the above-identified patent and that said Letters Patent is hereby corrected as shown below:

Substitute drawing Figure 1, as attached hereto, for drawing Figure 1.

Substitute drawing Figure 5, as attached hereto, for drawing Figure 5.

Substitute drawing Figure 6, as attached hereto, for drawing Figure 6.

Substitute drawing Figure 10, as attached hereto, for drawing Figure 10.

Substitute drawing Figure 11, as attached hereto, for drawing Figure 11.

Substitute drawing Figure 12, as attached hereto, for drawing Figure 12.

Signed and Sealed this

Fourth Day of April, 2000

Attest:

Q. TODD DICKINSON

*Attesting Officer*  *Director of Patents and Trademarks*

```
1   CAGGTGCAGCTGCAGGAGTCGGGCCCAGGACTGGTGAAGCCTTCGGAGACCCTGTCCGTC    60
    Q  V  Q  L  Q  E  S  G  P  G  L  V  K  P  S  E  T  L  S  V

61  ACCTGCACTGTCTCTGGTGGCTCCGTCAGTAGTTCCTACTGGAGCTGGATCCGGCAGCCC   120
    T  C  T  V  S  G  G  S  V  S  S  S  Y  W  S  W  I  R  Q  P
                                  <———— CDR1 ————>

121 CCAGGGAAGGGACCGGAGTGGATTGGGTATATCTATTACAGTGGGAGCACCAACTACAAC   180
    P  G  K  G  P  E  W  I  G  Y  I  Y  Y  S  G  S  T  N  Y  N
                                     <———————— CDR2

181 CCCTCCCTCAGGAGTCGAGTCACCATATCAGTAGACACGTCCAAGAACCAGTTCTCCCTG   240
    P  S  L  R  S  R  V  T  I  S  V  D  T  S  K  N  Q  F  S  L
    ————>

241 AAGCTGGGCTCTGTGACCGCTGCGGACACGGCCGTGTATTACTGTGCGAGAGTTTTGGTT   300
    K  L  G  S  V  T  A  A  D  T  A  V  Y  Y  C  A  R  V  L  V
                                                           <———

301 TCCCGTACGATTCACAGTACTCCTATTACATGGACGTCTGGGGCAAAGGGACCACGGTC   360
    S  R  T  I  S  Q  Y  S  Y  Y  M  D  V  W  G  K  G  T  T  V
    —— CDR3 ——————————————————————>

361 ACCGTGTCCTCA   372
    T  V  S  S
```

FIG. 5

```
1   ──────PCR PRIMER──────CGCAGGACTGTGAAGCCTTCGGAGACCCTGTCCCTC  60
                        .   A  G  L  L  K  P  S  E  T  L  S  L

61  ACCTGCGCTGTCTATGGTGGGTCCTTCAGTGGTTACTACTGGAGCTGGATCCGCCAGCCT 120
     T  C  A  V  Y  G  G  S  F  S  G  Y  Y  W  S  W  I  R  Q  P
                                     <────── CDR1 ──────>

121 CCAGGGAAGGGGCTGGAGTGGATTGGGGAAATCAATCATAGTGGAAGGACCAACTACAAC 180
     P  G  K  G  L  E  W  I  G  E  I  N  H  S  G  R  T  N  Y  N
                                 <──────────── CDR2

181 CGGTCCCTCAAGACTCGAGTCACCATATCAGTAGACACGTCCAAGAACCAGTTCTCCCTG 240
     R  S  L  K  T  R  V  T  I  S  V  D  T  S  K  N  Q  F  S  L
     ──────>

241 AAGCTGAGTTCTGTGACCGCCGCGGACACGGCTGTGTATTACTGTGCGAGACTGTGGCTC 300
     K  L  S  S  V  T  A  A  D  T  A  V  Y  Y  C  A  R  L  W  L
                                                       <──────

301 GATGGACATGGGTACAAGTTTGACTACTGGGGCCAGGGAACCCT──────PCR PRIMER── 360
     D  G  H  G  Y  K  F  D  Y  W  G  Q  G  T  L  .  .  .  .
     ──────────── CDR3 ──────>
```

FIG. 6

```
1    ————PCR PRIMER————GGGAGGCGTGGTCCAGCCTGGGAGGTCCTGAGACTC      60
                                G  G  V  V  Q  P  G  R  F  L  R  L

61   TCCTGTGCAGCGTCTGGATTCACCTTCAGTAGCTATGGCATGCACTGGGTCCGCCAGGCT 120
      S  C  A  A  S  G  F  T  F  S  S  Y  G  M  H  W  V  R  Q  A
                                      <————CDR1————>

121  CCAGGCAAGGGGCTGGAGTGGGTGGCACTTATATGGTATGATGGAAGTAATAAAGAATAT 180
      P  G  K  G  L  E  W  V  A  L  I  W  Y  D  G  S  N  K  E  Y
                                   <————CDR2

181  GCAGACTTCGTGAAGGGCCGATTCACCATCTCCAGAGACAATTCCAAGAATACACTGTAT 240
      A  D  F  V  K  G  R  F  T  I  S  R  D  N  S  K  N  T  L  Y
                                ————>

241  CTGCAAATGAACAGCCTGAGAGCCGAGGACACGGCTGTGTATTACTGTGCGACAGATAGT 300
      L  Q  M  N  S  L  R  A  E  D  T  A  V  Y  Y  C  A  T  D  S
                                                         <————

301  CCCAAAATGAGGGCTGGAAGTATGTTTCGCTACTACTACATGGACGTCTGGGGCAAAGGG 360
      P  K  M  R  A  G  S  M  F  R  Y  Y  Y  M  D  V  W  G  K  G
     ————————————————CDR3————————————————>

361  ACCAC ————PCR PRIMER————  381
      T
```

FIG. 10

```
  1  ———PCR PRIMER——————— GGGAGGCTTAGTTCAGCCTGGGGGTCCCTGAGACTC    60
                               G  G  L  V  Q  P  G  G  S  L  R  L

61  TCCTGTGCAGCCTCTGGATTCACCTTCAGTAGTTACTGGATGCACTGGGTCCGCCAAGCT   120
      S  C  A  A  S  G  F  T  F  S  S  Y  W  M  H  W  V  R  Q  A
                                        <———— CDR1 ————>

121  CCAGGGAAGGGGCTGGTGTGGGTCTCACGTATTAATAGTTATGGAATTAGCACAAGTTAC   180
      P  G  K  G  L  V  W  V  S  R  I  N  S  Y  G  I  S  T  S  Y
                                     <———————— CDR2

181  GCGAACTCCGTGAAGGGCCGATTCACCATCTCCAGAGACAACGCCAAGAACACGCTGTAT   240
      A  N  S  V  K  G  R  F  T  I  S  R  D  N  A  K  N  T  L  Y
     ————————>

241  CTGCAAATGAACACACTCTGAGAGCCGAGGACACGGCTGTATATTACTGTGCAAGAGGAGAG   300
      L  Q  M  N  T  L  R  A  E  D  T  A  V  Y  Y  C  A  R  G  E
                                                              <——

301  CGCATAGCAGCTCGTCTCTTGTCGGGGGTACGTGGACGTCTGGGGGCCAAGGGACC       360
      R  I  A  A  R  L  L  S  G  G  Y  G  M  D  V  W  G  Q  G  T
     ———————— CDR3 ————————>

361  AC ————PCR PRIMER——— 378
```

FIG. 11

```
1   ────PCR PRIMER────  GGGAGGCGTGGTCCAGCCTGGGAGGTCCCTGAGACTC   60
                         G  G  V  V  Q  P  G  R  S  L  R  L

61  TCCTGTGCAGCCTCTGGATTCACCTTTAGTAGCTATGGCATGCACTGGGTCCGCCAGGCT  120
     S  C  A  A  S  G  F  T  F  S  S  Y  G  M  H  W  V  R  Q  A
                                         <──── CDR1 ────>

121 CCAGGCAAGGGGCTGGAGTGGGTGGCAGTGATATGGTATGATGGAAGTAATAAGTACTAT  180
     P  G  K  G  L  E  W  V  A  V  I  W  Y  D  G  S  N  K  Y  Y
                                <──────────── CDR2

181 GCAGAGTCCGTGAAGGGCCGATTCACCATCTCCAGAGACAACTCCAAGAACACGCTGTAT  240
     A  E  S  V  K  G  R  F  T  I  S  R  D  N  S  K  N  T  L  Y
     ────>

241 CTGCAAATGAACAGCCTGAGAGCCGAGGACACGGCTGTGTATTACTGTGCGAGAGTCGTT  300
     L  Q  M  N  S  L  R  A  E  D  T  A  V  Y  Y  C  A  R  V  V
                                                              <────

301 AGCAGCAACCGGTACTCTCTAAGCTACTATTATTACTACTATGGACGTCTGGGGCAAAGGG  360
     S  S  N  R  Y  S  L  S  Y  Y  Y  Y  Y  Y  M  D  V  W  G  K  G
     ──────────────────── CDR3 ────────────────────>

361 ACCAC   ────PCR PRIMER────   381
     T
```

FIG. 12